(12) United States Patent
Kazuno et al.

(10) Patent No.: US 8,642,572 B2
(45) Date of Patent: Feb. 4, 2014

(54) CYTIDINE DERIVATIVE-CONTAINING ANTITUMOR AGENT FOR CONTINUOUS INTRAVENOUS ADMINISTRATION

(75) Inventors: Hiromi Kazuno, Hanno (JP); Katsuhisa Koizumi, Tokushima (JP); Akira Mita, Chiyoda-ku (JP)

(73) Assignee: Taiho Pharmaceutical Co., Ltd., Tokyo (JP)

(*) Notice: Subject to any disclaimer, the term of this patent is extended or adjusted under 35 U.S.C. 154(b) by 196 days.

(21) Appl. No.: 12/594,823

(22) PCT Filed: Apr. 4, 2008

(86) PCT No.: PCT/JP2008/000874
§ 371 (c)(1),
(2), (4) Date: Oct. 6, 2009

(87) PCT Pub. No.: WO2008/126398
PCT Pub. Date: Oct. 23, 2008

(65) Prior Publication Data
US 2010/0120709 A1 May 13, 2010

(30) Foreign Application Priority Data
Apr. 6, 2007 (JP) .................................. 2007-100676

(51) Int. Cl.
*A61K 31/7068* (2006.01)
*C07H 19/067* (2006.01)

(52) U.S. Cl.
CPC .......... *A61K 31/7068* (2013.01); *C07H 19/067* (2013.01)
USPC ........................................... 514/49; 536/28.5

(58) Field of Classification Search
None
See application file for complete search history.

(56) References Cited

PUBLICATIONS

Guidance for Industry Estimating the Maximum Safe Starting Dose in Initial Clinical Trials for Therapeutics in Adult Healthy Volunteers, published by U.S. Department of Health and Human Services, Food and Drug Administration, Jul. 2005, 30 pages.*
"Cancer Treatment", Merck Manual Online Edition, [retrieved on Feb. 21, 2012]. Retrieved from the Internet http://www.merckmanuals.com/home/. Revision Nov. 2008.*
Tabata, Satoshi et al., "Antitumor effect of a novel multifunctional antitumor nucleoside 3'—ethynylcytidine, on human cancers", Oncology Reports, vol. 3, No. 6, pp. 002/27-007/027, (1996).
Tanaka, Motoshiro et al., "Antitumor Effect and Mechanism of a Novel Multifunctional Nucleoside, 3'-Ethynylnucleosides, on Human Cancers", Japanese Journal of Cancer and Chemotherapy, vol. 24, No. 4, pp. 476-482, (Feb. 1997), (with English abstract).
Ota, Kazuo, "Symposium on diagnosis and treatment of cancer, Recent progress. II. Treatment of cancer 1. Recent cancer chemotherapy", The Journal of the Japanese Society of Internal Medicine/ The 84th meeting, vol. 76, No. 11, pp. 1658-1662, (1987), (with partial English translation).
Warrell, Raymond P., Jr. et al., Treatment of patients with advanced malignant lymphoma using gallium nitrate administered as a seven-day continuous infusion, American Cancer Society, vol. 51, No. 11, pp. 1982-1987, (Jun. 1, 1983).
Posner, Marshall R. et al., "Phase I study of continuous-infusion cisplatin", Cancer Treatment Reports, vol. 70, No. 7, pp. 847-850, (Jul. 1986).
U.S. Appl. No. 12/934,772, filed Sep. 27, 2010, Kazuno.
Hideshi Hattori, et al., "Nucleosides and Nucleotides. 158. 1-(3-C-Ethynyl1-β-D-*ribo*-pentofuranosyl)—cytosine, 1-(3-C-Ethynyl1-β-D-ribo-pentofuranosyl)uracil, and Their Nucleobase Analogues as New Potential Multifunctional Antitumor Nucleosides with a Broad Spectrum of Activity[1]" J. Med. Chem., vol. 39, 1996, pp. 5005-5011.
Yuji Shimamoto, et al., "Antitumor Activity and Pharmacokinetics of TAS-106, 1-(3-*C*-Ethynyl1-β-D-ribo-pentofuranosyl)cytosine", Jpn. J. Cancer Res., vol. 92, Mar. 2001, pp. 343-351.
M. Thomas, et al., "A phase 1 and pharmacokinetic study of TAS-106 administered weekly for 3 consecutive weeks every 28 days in patients with solid tumors", EORTC-NCI-AACR Symposium, Poster Sessions 67A, Nov. 20, 2002, 1 page abstract.
L. Hammond, et al., "Phase I and pharmacokinetic (PK) Trial of 3'-C-ethylnylcytidine (TAS-106) in solid tumors", EORTC-NCI-AACR Symposium, Poster Sessions 364, Nov. 21, 2002, 1 page abstract.
Extended European Search Report issued Jul. 20, 2011, in Patent Application No. 08738486.3.
Satoshi Takatori, et al: "Antitumor mechanisms and metabolism of the novel antitumor nucleoside analogues, 1-(3-C-ethynyl-[beta]-D-ribo-pentofuranosyl) cytosine and 1-(3-C-ethynyl-[beta]-D-ribo-pentofuranosyl) uracil" , Cancer Chemotherapy and Pharmacology 1999 DE Lnkd-DOI:10.1007/S002800050952, vol. 44, No. 2, 1999, pp. 97-104, XP002649139, ISSN:0344-5704.
Atsushi Azuma, et al: "1-(3-C-ethynyl-[beta]-D-ribo-pentofuranosyl) cytosine (ECyd, tas-106)1: Antitumor effect and mechanism of action", Nucleosides, Nucleotides and Nucleic Acids 2001 US Lnkd-DOI:10.1081/NCN-100002337, vol. 20, No. 4-7, 2001, pp. 609-619, XP002649140, ISSN:1525-7770.
Hiromi Kazuno, et al: "possible antitumor activity of 1-(3-C-ethynyl-[beta]-D-ribo-pentofuranosyl) cytosine (ECyd, tas-106) against an established gemcitabine (dFdCyd)- resistant human pancreatic cancer cell line", Cancer Science, vol. 96, No. 5, May 2005, pp. 295-302, XP002649141, ISSN:1347-9032.
FDA US Food and Drug Administration: "Oncology Tools: Dose calculator", Jul. 5, 2011, XP002649142, Retrieved from the Internet: URL:http://www.accessdata.fda.gov/scripts/cder/onctools/animalresults.cfm[retrieved on Jul. 5, 2011].
Office Action issued on Feb. 15, 2012 for Russian Patent Application No. 2009140983 (with English translation).

(Continued)

*Primary Examiner* — Eric S Olson
(74) *Attorney, Agent, or Firm* — Oblon, Spivak, McClelland, Maier & Neustadt, L.L.P.

(57) ABSTRACT

A method for administering ECyd to a patient that realizes a continuous therapy without expressing peripheral neurotoxicity caused by ECyd and that exhibits an excellent therapeutic effect and prolongs patient survival. An antitumor agent containing ECyd or a salt thereof and a method of administering it to a cancer patient through continuous intravenous administration at a dose of 1.30 to 8.56 mg/m$^2$ in terms of ECyd, for each administration period of 2 to 336 hours.

12 Claims, 3 Drawing Sheets

(56) References Cited

PUBLICATIONS

Fisenko V.P. et al. Manual for experimental (preclinical) study of novel pharmacological compounds, Mosco. 2000. p. 98 (with English translation).
Cappuzzo, et al., Lung Cancer (2006) 52, 319-325.
Colly, et al., Med. Pediatr Oncol. 1982; 10 Suppl 1:209-19.
Inoue, et al., Cancer Chemother, Pharmacol. 2004; 53(5): 415-22 (Abstract).
Takimoto, C.H., et al. Phase I evaluation of a 24-h infusion of TAS-106 every 3 weeks (wks) in patients (pts) with solid tumors. An abstract of 2007 ASCO Annual Meeting Proceedings (J.Clin.Oncol., 25918S), 2007, 2513.
Takimoto, C.H., et al. Phase I evaluation of a 24-h infusion of TAS-106 every 3 weeks (wks) in patients (pts) with solid tumors. A presentation sheet (MS Power Point Data) used in the ASCO 2007 ASCO Annual Meeting Proceedings (J.Clin.Oncol., 25918S), 2007, 2513.

* cited by examiner

CYTIDINE DERIVATIVE-CONTAINING ANTITUMOR AGENT FOR CONTINUOUS INTRAVENOUS ADMINISTRATION

TECHNICAL FIELD

The present invention relates to an antitumor agent which is continuously administered intravenously to cancer patients.

BACKGROUND ART 1-(3-C-Ethynyl-β-D-ribopentofuranosyl)cytosine (ECyd, represented by the following formula) is a novel antimetabolite having a structure in which the 3'-β-position of the ribose of cytidine is substituted by an ethynyl group.

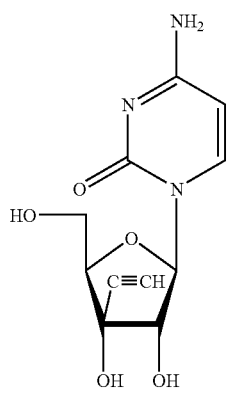

[F1]

ECyd is a cytidine analogue which was first synthesized in Japan. Differing from a pyrimidine derivative (5-FU) or a deoxycytidine derivative (gemcitabine), which are antitumor agents generally employed in the clinical settings, ECyd weakly acts on DNA and mainly inhibits RNA synthesis. Specifically, in a proposed mechanism, ECyd is phosphorylated by intracellular uridine/cytidine kinase, to thereby form a triphosphate (ECTP), which inhibits RNA polymerases I, II, and III, leading relevant cells to death.

Many antitumor agents which are generally employed in the clinical settings and which work based on DNA synthesis inhibition as a main action exhibit the inhibitory effect in an S-phase. Tumor cells employed in animal tests generally exhibit relatively fast proliferation. However, studies have revealed that, in the clinical settings, tumor cells proliferate at a slow rate, and a small number of the cells are in the S-phase. Since, differing from DNA synthesis inhibiting agents, the antitumor effect of ECyd based on RNA synthesis inhibitory action is not affected by the cell cycle of tumor cells, ECyd is thought to serve as a clinically useful antitumor agent, which differs from DNA synthesis inhibiting agents generally employed in the clinical settings.

ECyd exhibits a potent antitumor effect on a wide range of tumors (Non-Patent Documents 1 and 2). In a tumor inhibition test employing animal models, ECyd was found to exhibit potent antitumor effect on a variety of human-derived tumor strains through rapid intravenous injection (i.e., bolus intravenous injection) once a week for two weeks (Non-Patent Document 3). In the animal models, virtually no significant adverse effects were observed at an effective ECyd dose which provides antitumor effect and, therefore, ECyd is a promising candidate for a useful agent in the clinical setting.

Meanwhile, a clinical phase I test of a cancer treatment agent containing ECyd as an active ingredient was performed in the United States. In the test, when ECyd was administered through rapid intravenous injection with a regimen of administration once every three weeks or a regimen of administration once a week for three weeks and a rest period for one week, a sufficient blood ECyd level was obtained. The test showed that ECyd has a tumor growth inhibitory action with respect to some multiple-cancer patients who cannot be treated by a conventional drug.

However, peripheral neurotoxicity was observed as a dose-limiting toxicity, rendering difficult a further increase in dose of ECyd for evaluation thereof as an antitumor agent and continuous administration of ECyd. Thus, the cancer therapeutic effect of ECyd is unsatisfactory in the clinical setting (Non-Patent Documents 4 and 5).

Non-Patent Document 1: J. Med. Chem., 39, 5005-5011, 1996
Non-Patent Document 2: Oncol. Rep., 3, 1029-1034, 1996
Non-Patent Document 3: Jpn. J. Cancer Res., 92, 343-351, 2001
Non-Patent Document 4: EORTC-NCI-AACR Symposium, Abs. 67A, 2002
Non-Patent Document 5: EORTC-NCI-AACR Symposium, Abs. 364, 2002

DISCLOSURE OF THE INVENTION

Problems to be Solved by the Invention

The present invention is directed to provision of a new method of using ECyd, which method attains high antitumor effect and involves low risk of expressing peripheral neurotoxicity.

Means for Solving the Problems

The present inventors have carried out extensive studies on use of ECyd, and have found that, through intravenous administration of ECyd over a long period of time to a patient, high antitumor effect can be attained, and toxicity can be reduced, making the administration method effective for prolonging the survival of the patient.

Accordingly, the present invention is directed to the following 1) to 7).

1) An antitumor agent containing ECyd or a salt thereof, which is administered to a cancer patient through continuous intravenous administration at a dose of 1.30 to 8.56 mg/m$^2$ as reduced to ECyd, for each administration period of 2 to 336 hours.

2) The antitumor agent as described in 1) above, wherein the administration period is 4 to 72 hours.

3) The antitumor agent as described in 1) above, wherein the administration period is 24 hours.

4) The antitumor agent as described in any of 1) to 3) above, which is administered at a dose of 2.80 to 8.56 mg/m$^2$ as reduced to ECyd.

5) The antitumor agent as described in any of 1) to 3) above, which is administered at a dose of 6.85 mg/m$^2$ as reduced to ECyd.

6) Use of 1-(3-C-ethynyl-β-D-ribopentofuranosyl)cytosine or a salt thereof for producing an antitumor agent, wherein the antitumor agent is administered to a cancer patient through continuous intravenous administration at a dose of 1.30 to 8.56 mg/m$^2$ as reduced to 1-(3-C-ethynyl-β-D-ribopentofuranosyl)cytosine, for each administration period of 2 to 336 hours.

7) A method for cancer treatment, comprising administering, to a cancer patient, an antitumor agent containing 1-(3-C-ethynyl-β-D-ribopentofuranosyl)cytosine or a salt thereof through continuous intravenous administration at a dose of 1.30 to 8.56 mg/m² as reduced to 1-(3-C-ethynyl-β-D-ribopentofuranosyl)cytosine, for each administration period of 2 to 336 hours.

Effects of the Invention

According to the antitumor agent of the present invention, high antitumor effect can be attained with reduced risk of expressing peripheral neurotoxicity. In other words, through a cancer treatment employing the antitumor agent, the survival of the patient can be surely prolonged, while reducing the risk of suspension of the treatment which would otherwise be caused by adverse effects.

Figure 1:
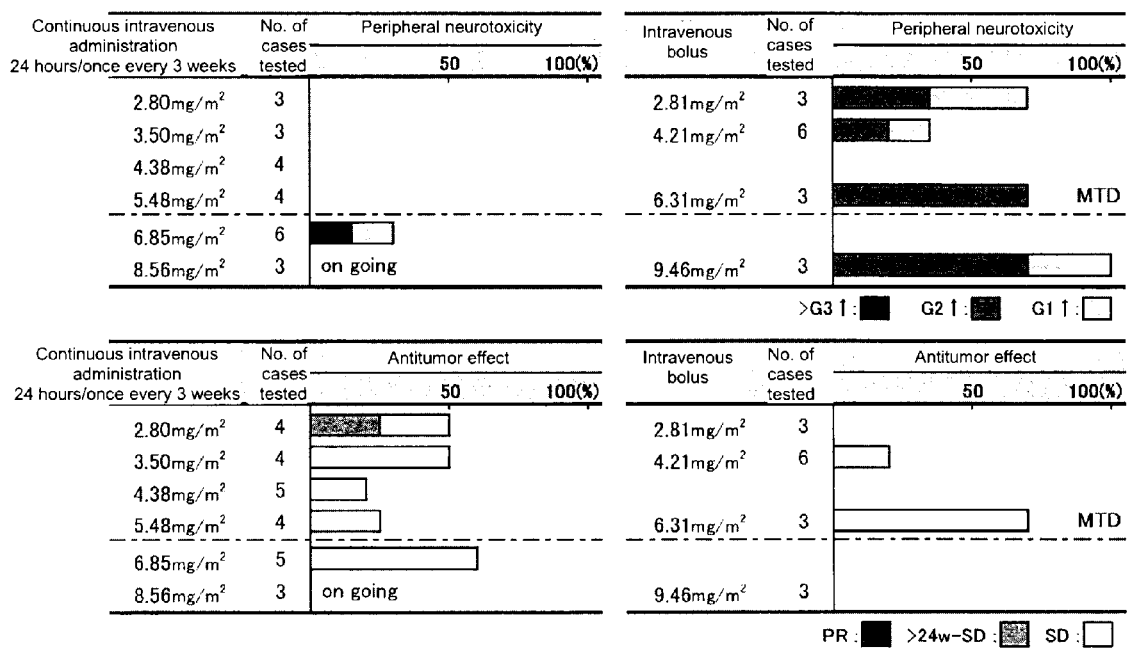
FIG. 1

Graphs showing the expression of neurotoxicity as a dose-limiting toxicity in cancer treatment and the efficacy of the therapy, when a formulation of ECyd is administered via rapid intravenous administration once every three weeks, or via continuous intravenous administration. (PR: partial response, SD: stable disease). The lateral axis represents the occurrence of onset of neurotoxicity (%) or that of therapeutic efficacy (%).

FIG. 2

A graph showing the effects of the ECyd contact schedule on growth inhibition of neural-crest-derived rat adrenal medulla chromaffin cells (PC12 strain).

FIG. 3

A graph showing the effects of the ECyd contact schedule on growth inhibition of human lung tumor cells (A549 strain). The legend in the upper right corner of FIG. 3 identifies A549 cell samples contacted with ECyd for various periods of time between 0.5 hr and 100 hr. The X axis shows the number of days of cell culture after ECyd-containing cell culture medium was replaced and the Y axis shows the amount of cell growth after the periods of contact with ECyd as determined by staining with Crystal Violet.

BEST MODES FOR CARRYING OUT THE INVENTION

ECyd, 1-(3-C-ethynyl-β-D-ribopentofuranosyl)cytosine, employed as an active ingredient of the antitumor agent of the present invention, is a known compound and is known to exhibit an antitumor effect to a variety of cancers through RNA synthesis inhibitory action. Notably, it has never been reported that cancer can be effectively treated with suppression of adverse effects through continuous intravenous administration of ECyd.

No particular limitation is imposed on the salt of ECyd, so long as it is pharmaceutically acceptable. Examples of the salt include inorganic acid salts such as hydrochlorides, hydrobromides, sulfates, nitrates, and phosphates; and organic acid salts such as acetates, propionates, tartrates, fumarates, maleates, malates, citrates, methanesulfonates, p-toluenesulfonates, and trifluoroacetates.

ECyd or a salt thereof employed in the present invention may be produced through a known method, for example, a method disclosed in JP-B-3142874.

The antitumor agent of the present invention is intravenously administered to patients, and the dosage form is an injection. The injection may be a liquid injection formulation or a solid injection formulation such as freeze-dried and powder injection formulations which can be reconstituted upon use.

The antitumor agent of the present invention may be prepared by adding ECyd or a salt thereof to a pharmacologically acceptable carrier and processing the mixture through a routine method. Examples of the carrier employed in the invention include organic and inorganic carriers generally employed as materials of drug formulations. Specifically, a excipient, a lubricant, a binder, a disintegrant, etc. may be added to a solid injection formulation, and a diluent, a solubilizing agent, a suspending agent, a tonicity agent, a pH-adjusting agent, a buffer, a stabilizer, a soothing agent, etc. may be added to a liquid injection formulation. If needed, additives for drug formulations such as an antiseptic agent, an antioxidant, and a coloring agent may also be employed.

Examples of the excipient include lactose, sucrose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerin, sodium alginate, gum arabic, and mixtures thereof. Examples of the lubricant include purified talc, stearate salts, borax, polyethylene glycol, and mixtures thereof. Examples of the binder include simple syrup, glucose liquid, starch liquid, gelatin solution, poly(vinyl alcohol), poly(vinyl ether), polyvinylpyrrolidone, carboxymethylcellulose, shellac, methylcellulose, ethylcellulose, water, ethanol, potassium phosphate, and mixtures thereof. Examples of the disintegrant include dry starch, sodium alginate, powdered agar, powdered laminaran, sodium hydrogencarbonate, calcium carbonate, polyoxyethylene sorbitan fatty acid esters, sodium lauryl sulfate, stearic monoglyceride, starch, lactose, and mixtures thereof. Examples of the diluent include water, ethyl alcohol, Macrogol, propylene glycol, ethoxylated isostearyl alcohol, polyoxylated isostearyl alcohol, polyoxyethylene sorbitan fatty acid esters, and mixtures thereof. Examples of the stabilizer include sodium pyrosulfite, ethylenediaminetetraacetic acid, thioglycolic acid, thiolactic acid, and mixtures thereof. Examples of the tonicity agent include sodium chloride, boric acid, glucose, glycerin, and mixtures thereof. Examples of the pH-adjusting agent and buffer include sodium citrate, citric acid, sodium acetate, sodium phosphate, and mixtures thereof. Examples of soothing agent include procaine hydrochloride, lidocaine hydrochloride, and mixtures thereof.

The dose of the antitumor agent of the present invention is determined in consideration of the balance between the risk of adverse effects and the antitumor effect. The dose thereof is preferably 1.30 to 8.56 mg/m² as reduced to ECyd, more preferably 2.80 to 8.56 mg/m², and particularly preferably 6.85 mg/m².

The antitumor agent of the present invention is administered to a cancer patient for each administration period of 2 to 336 hours via continuous intravenous administration. In consideration of the balance between the risk of adverse effects and the antitumor effect, the administration time is more preferably 4 to 72 hours, particularly preferably 24 hours.

Through continuous intravenous administration for such a long time, the target cancer can be effectively treated, with suppression of onset of adverse effects such as peripheral neurotoxicity.

In continuous intravenous administration of the antitumor agent of the present invention, a specific administration regimen serving as one course is preferably repeated in order to attain higher antitumor effect with suppression of peripheral neurotoxicity. The administration regimen is preferably continuous intravenous administration once every one to three weeks, more preferably once every three weeks.

In one preferred administration regimen of the antitumor agent of the present invention, a course including a 24-hour continuous intravenous administration once every three weeks at a dose of 1.30 to 8.56 mg/m² as reduced to ECyd for each administration is performed once or a plurality of times. In another preferred administration regimen, a course including a 4-hour continuous intravenous administration once every three weeks out of a continuous four-week period at a dose of 1.30 to 8.56 mg/m² as reduced to ECyd for each administration is performed once or a plurality of times. In a more preferred administration regimen, a course including a 24-hour continuous intravenous administration once every three weeks at a dose of 6.85 mg/m² as reduced to ECyd for each administration is performed once or a plurality of times. In another, more preferred administration regimen, a course including a 4-hour continuous intravenous administration once every three weeks out of a continuous four-week period at a dose of 1.30 mg/m² as reduced to ECyd for each administration is performed once or a plurality of times.

No particular limitation is imposed on the cancer to which the antitumor agent of the present invention is applied. Examples of the cancer include head and neck cancer, esophageal cancer, stomach cancer, colorectal cancer, liver cancer, gallbladder/bile duct cancer, pancreatic cancer, lung cancer, breast cancer, ovarian cancer, bladder cancer, prostate cancer, testicular tumor, bone and soft tissue sarcoma, malignant lymphoma, leukemia, cervical cancer, skin cancer, and brain tumor. Among them, head and neck cancer, lung cancer, stomach cancer, colorectal cancer, pancreatic cancer, and breast cancer are particularly preferred.

The cancer patient to whom the antitumor agent of the present invention is administered may be a cancer patient who had received no cancer treatment, a cancer patient who is currently receiving a cancer treatment, or a cancer patient who has ever received a cancer treatment.

The antitumor agent of the present invention may be employed in combination with another antitumor agent or radiation. Examples of the antitumor agent which can be used in combination include 5-FU, tegafur-uracil formulation, tegafur-gimeracil-oteracil potassium formulation, doxorubicin, epirubicin, irinotecan hydrochloride, etoposide, docetaxel, paclitaxel, cisplatin, carboplatin, oxaliplatin, krestin, lentinan, and picibanil.

EXAMPLES

The present invention will next be described in detail by way of examples, which should not be construed as limiting the invention thereto.

Example 1

A group of cancer patients was repeatedly subjected to a course including a 24-hour continuous intravenous administration once every three weeks at a dose of 2.80 to 8.56 mg/m² as reduced to ECyd for each administration. Another group of cancer patients was repeatedly subjected to a course including a rapid intravenous administration once every three weeks at a dose of 2.81 to 9.46 mg/m² as reduced to ECyd. In both cases, the neurotoxicity occurrence and the therapeutic effect by ECyd were investigated.

The above test is equivalent to the phase I clinical trial, which is performed mainly for evaluating safety of the tested drug and determining the recommended dose (RD) of the drug, which ensures safety of the drug without adverse effects in the phase II clinical trial carried out with respect to the target cancer. The test is carried out for patients of solid cancers (e.g., gastrointestinal cancers, head and neck cancer, and breast cancer) which cannot be cured by a standard therapeutic method or to which no effective method is applicable. When the test is performed, if possible, the therapeutic effect on the target tumor is assessed. In the following examples, the therapeutic effect on the target tumor was assessed in accordance with the RECIST method (see Journal of the National Cancer Institute, 2000, Vol. 92, No. 3, p. 205 to 216). The effect of ECyd on shrinkage of the tumor was confirmed generally from a target lesion (a lesion having a size equal to or greater than the measurable size depending on the slice width obtained through CT or similar means) and the non-target lesions (all lesions other than the target lesion). In the above test, PR (partial response) refers to a state in which the sum of the longer diameters of target lesions was reduced by 30% or more as compared with that obtained before drug administration, the effect of shrinkage was maintained for a certain period (generally four weeks), and no exacerbation was observed in the non-target lesions during the test. PD (progressive disease) refers to a state in which the sum of the longer diameters of target lesions was increased by 20% or more as compared with the minimum sum of the longer diameters recorded after start of the test, or a state in which clear exacerbation in the non-target lesions or a new lesion was observed. SD (stable disease) refers to a state in which the degree of tumor shrinkage cannot be evaluated as PR and which cannot be evaluated as PD, and in which the tumor progress has stopped and no exacerbation was observed. MR (minor response) refers to a case in which a certain tumor shrinkage degree of about 15% was maintained (although it was less than 30%), or in which a therapeutic effect corresponding to PR is temporarily observed. FIG. 1 shows the results.

FIG. 1 shows the results of administration of an ECyd formulation (injection) once every three weeks at a dose of 2.80 to 9.46 mg/m² via rapid intravenous administration and results of 24-hour continuous intravenous administration. In the case of rapid intravenous administration, two of the three cases (66%) in which a dose of 2.81 mg/m² was employed exhibited peripheral neurotoxicity, and no therapeutic effect was observed. When the dose was increased to 6.31 mg/m², two of the three cases exhibited peripheral neurotoxicity, and a therapeutic efficacy (SD or higher) was observed in two of the three cases. In contrast, when continuous intravenous administration was carried out, at a dose of 2.80 mg/m² to 5.48 mg/m², no peripheral neurotoxicity was observed, and the therapeutic efficacy (SD or higher) was found to be 20 to 50%.

Therefore, continuous intravenous administration of ECyd has been considered to be a method which exhibits high therapeutic efficacy to patients of solid cancers (e.g., gastrointestinal cancers, head and neck cancer, and breast cancer) which cannot be cured by a standard therapeutic method or to which no effective method is applicable, while onset of peripheral neurotoxicity is suppressed.

Example 2

A course including a 4-hour continuous intravenous administration once every three weeks out of a continuous four-week period at a dose of 1.30 mg/m² as reduced to ECyd for each administration was repeatedly performed. Also, a course including a rapid intravenous administration once every three weeks out of a continuous four-week period at a dose of 1.32 mg/m² as reduced to ECyd was repeatedly performed. In both cases, the neurotoxicity occurrence and the therapeutic effect by ECyd were investigated. In Example 2, selection of the patients and the method and ratings of evaluation were the same as employed in Example 1.

The test results are as follows. In the case of rapid intravenous administration, one of the three cases (33%) exhibited peripheral neurotoxicity, and no therapeutic efficacy (SD or higher) was observed. In contrast, when continuous intravenous administration was carried out, peripheral neurotoxicity was observed in one of the three cases (33%), but the therapeutic efficacy (SD or higher) was found to be 66%.

Therefore, continuous intravenous administration of ECyd has been considered to be a method which exhibits high therapeutic efficacy to patients of solid cancers (e.g., gastrointestinal cancers, head and neck cancer, and breast cancer) which cannot be cured by a standard therapeutic method or to which no effective method is applicable, while onset of peripheral neurotoxicity is suppressed.

Example 3

The effects of the ECyd contact schedule on growth inhibition of neural-crest-derived rat adrenal medulla chromaffin cells (PC12 strain) were investigated.

Figure 2:
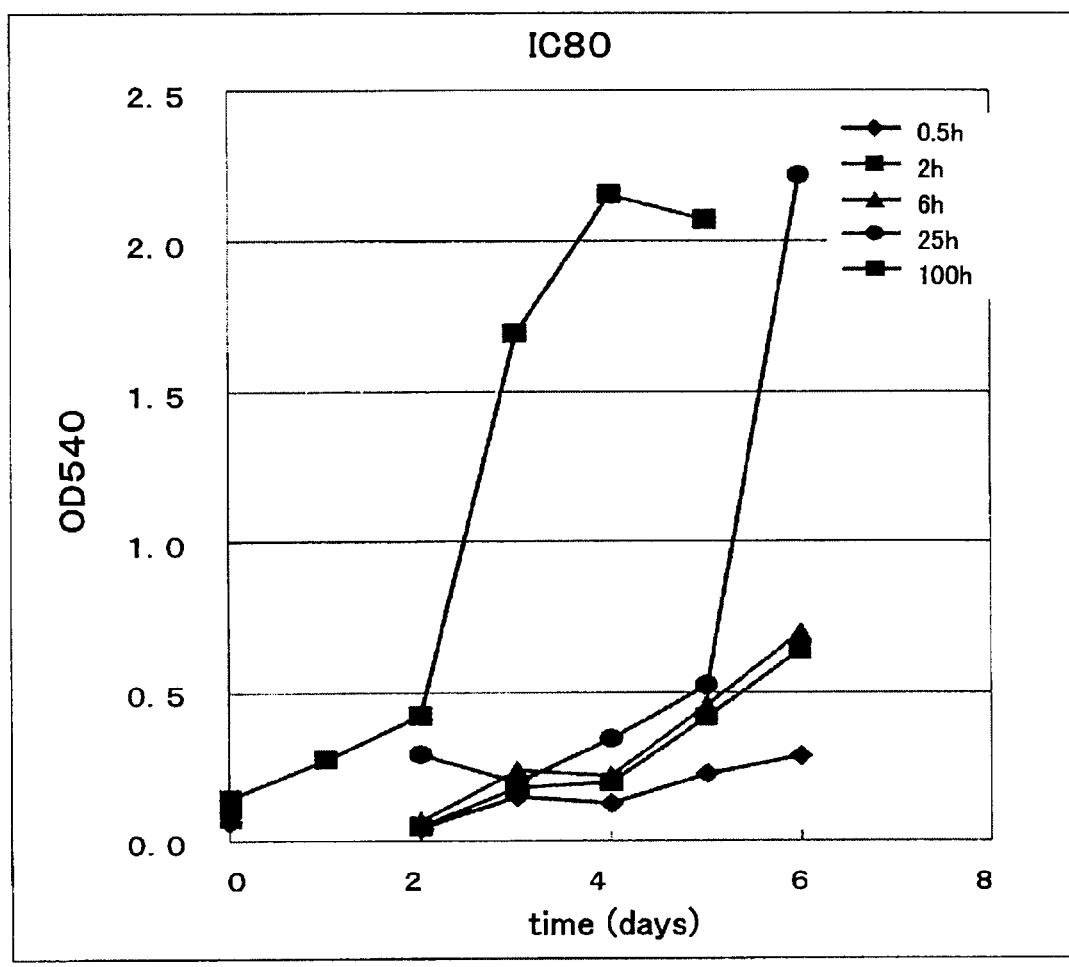

The experiment of Example 3 was performed at a constant AUC (product of contact time and ECyd concentration). Specifically, in each tested regimen, AUC was maintained at such a level that the ECyd concentration was adjusted to provide IC80 (0.08 μM) as a result of contact between ECyd and the PC12 cells for 100 hours. In each tested regimen, PC12 cells were seeded on a plate and treated with ECyd. Subsequently, the cell culture liquid was exchanged. The profile of cell growth thereafter was obtained through staining with Crystal Violet. FIG. 2 shows the results.

In the case of a contact time of 0.5 hours, growth of PC12 cells was virtually unrestored on day 6. In the cases of contact times of 25 and 100 hours, growth of PC12 cells was restored. The restoration of the cell growth was more rapidly attained, as the contact time was longer. Thus, inhibition of growth of neuronal cells PC12 was found to be more susceptible to Cmax, and the inhibition was not more significant in the case of contact of low-concentration ECyd for a long period of time than in the case of contact of high-concentration ECyd for a short period of time.

Therefore, the effect of continuous administration of ECyd on inhibition of neuronal cell growth was found to be not significant.

Example 4

The effects of the ECyd contact schedule on growth inhibition of human lung tumor cells (A549 strain) were investigated.

Figure 3:
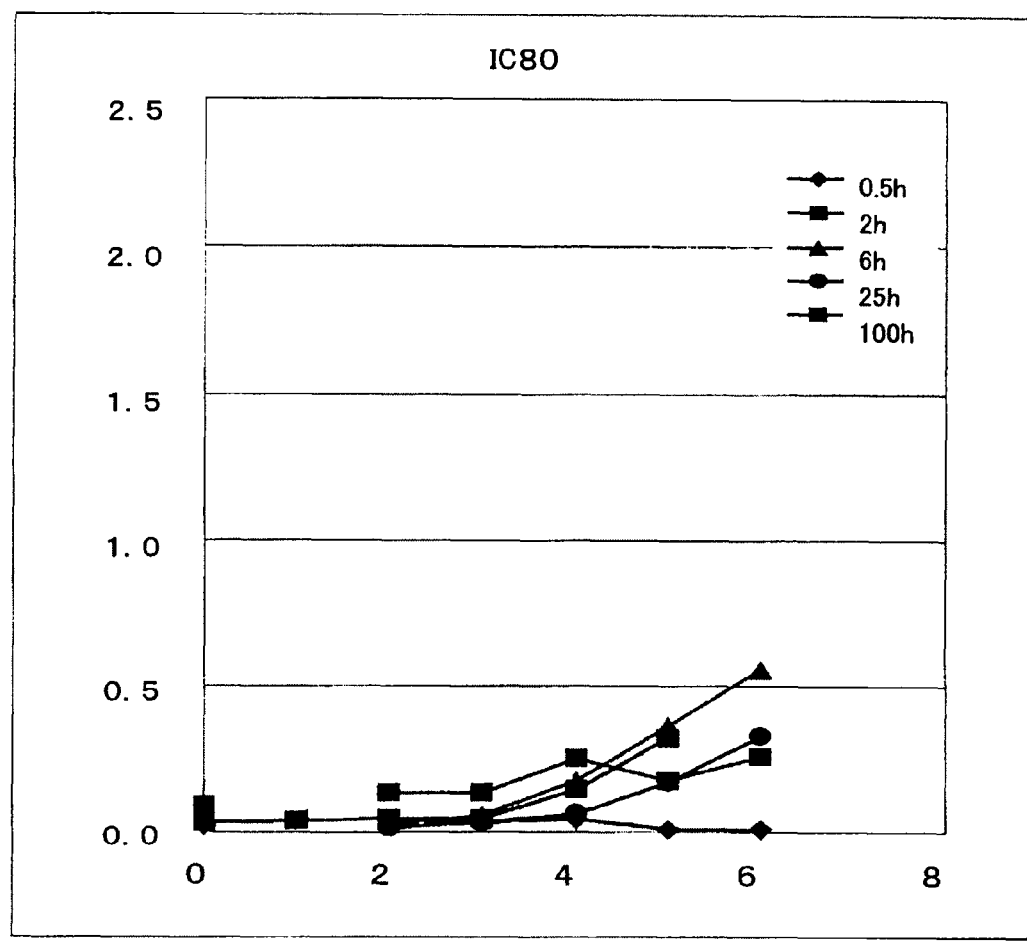

The experiment of Example 4 was performed at a constant AUC (product of contact time and ECyd concentration). Specifically, in each tested regimen, AUC was maintained at such a level that the ECyd concentration was adjusted to provide IC80 (0.08 μM) as a result of contact between ECyd and the A549 cells for 100 hours. In each tested regimen, A549 cells were seeded on a plate and treated with ECyd. Subsequently, the cell culture liquid was exchanged. The profile of cell growth thereafter was obtained through staining with Crystal Violet. FIG. 3 shows the results.

In the cases of contact times of 0.5 to 100 hours, growth of A549 cells was virtually unrestored on day 6. Thus, the tumor cell growth inhibition was found to be not influenced by Cmax.

Therefore, continuous administration of ECyd was found to attain a tumor cell growth inhibitory effect equivalent to that provided by rapid administration.

As described hereinabove, the continuous administration of ECyd according to the present invention was found to be a effective cancer therapy which exhibits high tumor cell growth inhibitory without causing peripheral neurotoxicity.

The invention claimed is:

1. A method of administering 1-(3-C-ethynyl-β-D-ribopentofuranosyl)cytosine ("ECyd") or a salt thereof to a subject in need thereof comprising:
   continuously intravenously administering to said subject for a period of 2 to 336 hours a dose of 1.30 to 8.56 mg/m$^2$ in terms of 1-(3-C-ethynyl-β-D-ribopentofuranosyl)cytosine; wherein said subject is a cancer patient who has a cancer or tumor susceptible to antitumor effects of ECyd.

2. The method according to claim 1, wherein the administration period is 4 to 72 hours.

3. The method according to claim 1, wherein the administration period is 24 hours.

4. The method according to claim 1, wherein said dose ranges from 2.80 to 8.56 mg/m$^2$.

5. The method according to claim 1, wherein said dose is 6.85 mg/m$^2$.

6. The method according to claim 1, wherein said subject is a cancer patient who has a solid cancer.

7. The method of claim 1, wherein said subject is a cancer patient who has head and neck cancer, lung cancer, stomach cancer, colorectal cancer, pancreatic cancer, or breast cancer.

8. The method of claim 1, further comprising administering one or more other anticancer agent(s).

9. A method for treating a subject having a tumor comprising:
   continuously intravenously administering to said subject for a period of 2 to 336 hours a dose of 1-(3-C-ethynyl-β-D-ribopentofuranosyl)cytosine that inhibits tumor cell growth but that does not cause peripheral neurotoxicity; wherein said tumor is susceptible to antitumor effects of ECyd.

10. A method for treating a subject in need of inhibition of RNA synthesis comprising:
    continuously intravenously administering to said subject for a period of 2 to 336 hours a dose of 1-(3-C-ethynyl-β-D-ribopentofuranosyl)cytosine that inhibits RNA synthesis but that does not cause peripheral neurotoxicity.

11. The method of claim 1, wherein peripheral neurotoxicity is reduced compared to that in an otherwise identical patient treated with ECyd administered in a bolus with a constant AUC (product of contact time and ECyd concentration).

12. The method of claim 1, wherein therapeutic efficacy of ECyd is at least as high as that in an otherwise identical patient treated with ECyd administered in a bolus with a constant AUC (product of contact time and ECyd concentration).

* * * * *